(12) United States Patent
Yumoto et al.

(10) Patent No.: US 8,524,397 B1
(45) Date of Patent: Sep. 3, 2013

(54) BATTERY HAVING HIGH RATE AND HIGH CAPACITY CAPABILITIES

(75) Inventors: Hiroyuki Yumoto, Stevenson Ranch, CA (US); Taison Tan, Glendora, CA (US); Nelly Bourgeon, Santa Clarita, CA (US); Hisashi Tsukamoto, Santa Clarita, CA (US); Lu Chow, Pasadena, CA (US)

(73) Assignee: Quallion LLC, Sylmar, CA (US)

( * ) Notice: Subject to any disclaimer, the term of this patent is extended or adjusted under 35 U.S.C. 154(b) by 1286 days.

(21) Appl. No.: 10/984,434

(22) Filed: Nov. 8, 2004

(51) Int. Cl.
*H01M 4/131* (2010.01)
*H01M 4/133* (2010.01)

(52) U.S. Cl.
USPC .................. 429/231.2; 429/231.7; 429/326

(58) Field of Classification Search
USPC .................. 429/231.7, 326, 231.2, 231.5
See application file for complete search history.

(56) References Cited

U.S. PATENT DOCUMENTS

| | | | |
|---|---|---|---|
| 3,514,337 A | 5/1970 | Braeuer et al. | |
| 3,536,532 A | 10/1970 | Watanabe et al. | |
| 3,892,590 A | 7/1975 | Gunther | |
| 3,922,174 A | 11/1975 | Heller | |
| 4,163,829 A | 8/1979 | Kronenberg | |
| 4,863,814 A | 9/1989 | Mohri et al. | |
| 4,931,240 A | 6/1990 | Tajima et al. | |
| 4,967,025 A | 10/1990 | Maeda et al. | |
| 5,175,066 A | 12/1992 | Hamwi et al. | |
| 5,180,642 A * | 1/1993 | Weiss et al. | 429/231.5 X |
| 5,478,671 A | 12/1995 | Idota | |
| 5,478,674 A | 12/1995 | Miyasaka | |
| 5,667,916 A | 9/1997 | Ebel et al. | |
| 5,707,756 A | 1/1998 | Inoue et al. | |
| 5,712,062 A | 1/1998 | Yamana et al. | |
| 5,716,422 A | 2/1998 | Muffoletto et al. | |
| 5,910,382 A | 6/1999 | Goodenough et al. | |
| 6,068,921 A | 5/2000 | Yamana et al. | |
| 6,136,477 A * | 10/2000 | Gan et al. | 429/307 |
| 6,211,065 B1 | 4/2001 | Xi et al. | |
| 6,232,021 B1 | 5/2001 | Negoro | |

(Continued)

FOREIGN PATENT DOCUMENTS

| | | |
|---|---|---|
| CA | 2200998 | 9/1998 |
| CA | 2270711 | 10/2000 |

(Continued)

OTHER PUBLICATIONS

R. Brec et al., Chemical and Electrochemical Study of the $Li_xFeS_2$ Cathodic System, Mater. Res. Bull., 1980, 15, 619-625.

(Continued)

*Primary Examiner* — Stephen J. Kalafut
(74) *Attorney, Agent, or Firm* — Gavrilovich, Dodd & Lindsey, LLP

(57) ABSTRACT

The battery has an electrolyte activating one or more anodes and one or more cathodes. At least one of the one or more cathodes includes or consists of one or more first active materials selected from the group consisting of: fluorinated carbon $(CF_x)$, $CuCl_2$, and $LiCuCl_2$; and includes or consists of one or more second active materials selected from the group consisting of lithium vanadium oxide, such as $Li_{1+y}V_3O_8$, where y is greater than zero and/or less than 0.3, $TiS_2$, polypyrrole, $MoO_2$, $MoS_2$, $MnO_2$, $V_2O_5$, $V_6O_{13}$, $H_2V_3O_8$, and metal vanadium oxides represented by $M_yH_{1-y}V_3O_8$ where $0<y\leq1$ and M represents Na, Mg, Ba, K, Co, and Ca and combinations thereof.

46 Claims, 2 Drawing Sheets

(56) References Cited

U.S. PATENT DOCUMENTS

| | | | |
|---|---|---|---|
| 6,332,900 | B1 | 12/2001 | Muffoletto et al. |
| 6,358,649 | B1 | 3/2002 | Yazami et al. |
| 6,383,688 | B1 | 5/2002 | Inagaki et al. |
| 6,432,584 | B1 | 8/2002 | Visco et al. |
| 6,514,640 | B1 | 2/2003 | Armand et al. |
| 6,589,696 | B2 | 7/2003 | Matsubara et al. |
| 6,692,865 | B2 | 2/2004 | Gan et al. |
| 6,787,268 | B2 | 9/2004 | Koike et al. |
| 6,986,796 | B2 * | 1/2006 | Warchocki et al. .......... 29/623.1 |
| 7,174,207 | B2 * | 2/2007 | Dodd et al. ........................ 607/5 |
| 7,226,704 | B2 | 6/2007 | Panitz et al. |
| 2002/0037450 | A1 | 3/2002 | Suzuki et al. |
| 2002/0039688 | A1 | 4/2002 | Barker et al. |
| 2002/0041997 | A1 | 4/2002 | Muffoletto et al. |
| 2002/0055047 | A1 | 5/2002 | Satoh et al. |
| 2002/0061446 | A1 | 5/2002 | Gan et al. |
| 2002/0061450 | A1 | 5/2002 | Tsujioka et al. |
| 2002/0064712 | A1 | 5/2002 | Sekino et al. |
| 2002/0086216 | A1 | 7/2002 | Sekino et al. |
| 2002/0090551 | A1 | 7/2002 | Gan et al. |
| 2002/0098410 | A1 | 7/2002 | Leysieffer et al. |
| 2002/0110739 | A1 | 8/2002 | McEwen et al. |
| 2002/0122973 | A1 | 9/2002 | Manev et al. |
| 2002/0136950 | A1 | 9/2002 | Gan et al. |
| 2002/0192137 | A1 | 12/2002 | Chaloner-Gill et al. |
| 2003/0138697 | A1 | 7/2003 | Leising et al. |
| 2003/0138698 | A1 | 7/2003 | Lee et al. |
| 2003/0194605 | A1 | 10/2003 | Fauteux et al. |
| 2004/0033360 | A1 | 2/2004 | Armand et al. |
| 2004/0034253 | A1 | 2/2004 | Angell et al. |
| 2004/0048156 | A1 * | 3/2004 | Thackeray et al. .... 429/231.2 X |
| 2004/0072075 | A1 | 4/2004 | Tsukamoto et al. |
| 2004/0163235 | A1 | 8/2004 | Feil et al. |
| 2004/0248014 | A1 * | 12/2004 | West et al. .................... 429/313 |
| 2007/0065726 | A1 | 3/2007 | Yumoto et al. |
| 2007/0065727 | A1 | 3/2007 | Koike et al. |

FOREIGN PATENT DOCUMENTS

| | | |
|---|---|---|
| DE | 10111410 C | 7/2002 |
| EP | 000886332 A1 | 12/1998 |
| EP | 0 910 547 B1 | 7/2001 |
| EP | 1 193 787 A2 | 4/2002 |
| EP | 1 207 567 A2 | 5/2002 |
| EP | 1 091 963 B1 | 10/2002 |
| JP | 58128657 A | 8/1983 |
| JP | 59083353 A | 5/1984 |
| JP | 61117503 A | 6/1986 |
| JP | 62188168 A | 8/1987 |
| JP | 01089144 A2 | 4/1989 |
| JP | 05047385 A2 | 2/1993 |
| JP | 05242910 A2 | 9/1993 |
| JP | 7335263 A2 | 12/1995 |
| JP | 10275619 A2 | 10/1998 |
| JP | 2000067905 A2 | 3/2000 |
| JP | 2001110414 | 4/2001 |
| JP | 2002063894 A2 | 2/2002 |
| JP | 2002141058 A2 | 5/2002 |
| JP | 2002-175836 A | 6/2002 |
| WO | WO 97/41061 A1 | 11/1997 |
| WO | WO 01/24305 A1 | 4/2001 |
| WO | WO 02/27823 A1 | 4/2002 |
| WO | WO 02/27824 A1 | 4/2002 |
| WO | WO 02/46101 A3 | 6/2002 |
| WO | WO 02/068432 A1 | 9/2002 |
| WO | WO 02/068433 A1 | 9/2002 |
| WO | WO 02/071528 A2 | 9/2002 |
| WO | WO 02/073716 A2 | 9/2002 |
| WO | WO 2004/023577 A2 | 3/2004 |

OTHER PUBLICATIONS

V.B. Nalbandyan, et al., New Modification of Lithium Monoferrite and the Morphotropic Series $AFeO_2$, Russian Journal of Inorganic Chemistry, 1987, 32, 3, 453-454.

A. Manthiram et al., Lithium Insertion into $Fe_2(MO_4)_3$ Frameworks: Comparison of M=W with M=Mo, Journal of Solid State Chemistry, 1987, 71, 349-360.

M. Endo et al.; Discharge characteristics of a lithium battery with fibrous carbon fluoride; Dialog Abstract for Elsevier; Journal of Power Sources; vol. 20, No. 1-2; pp. 99-104; 1987; Switzerland.

R.W. Pekela, Organic Aerogels From the Polycondensation of Resorcinol with Formaldehyde, Journal of Materials Science, 1989, 24, 3221-3227.

M. Endo et al.; Lithium primary battery with high electrical potential using fluorinated graphite fibers of second-stage intercalation; Dialog Abstract for Elsevier; Electrical Engineering in Japan; col. 110, No. 7; pp. 13-21; 1990; US.

A.K. Padhi et al., Phospho-olivines as Positive-Electrode Materials for Rechargeable Lithium Batteries, J. Electrochem. Soc., 1997, 144, 4, 1188-1194.

A.K. Padhi et al., Effect of Structure on the $Fe^{3+}/Fe^{2+}$ Redox Couple in Iron Phosphates, J. Electrochem. Soc., 1997, 144, 5, 1609-1613.

H. Momose et al.; X-ray photoelectron spectroscopy analyses of lithium intercalation and alloying reaction son graphite electrodes; Journal of Power Sources; vol. 68; pp. 208-211; 1997.

L. Ping et al.; Fabrication of LiV/sub 2/O/sub 5/ thin-film electrodes for rechargeable lithium batteries; Dialog Abstract for Elsevier; Solid State Ionics; col. 111, No. 1-2; pp. 145-151; 1998; Netherlands.

Huang et al., Approaching Theoretical Capacity of $LiFePO_4$ at Room Temperature at High Rates, Electrochemical and Solid-State Letters, 2001, 4(10), A170-A172.

J. Suzuki et al.; Li mass transfer through a metallic copper film on a carbon fiber during the electrochemical insertion/extraction reaction; Electrochemical and Solid State Letters; vol. 4(1); pp. A1-A4; 2001.

S. Kim et al.; Electrochemical performance of natural graphite by surface modification using aluminum; Electrochemical and Solid State Letters; vol. 4(8); pp. A109-A112; 2001.

S. Yang et al., Reactivity, Stability and Electrochemical Behavior of Lithium Iron Phosphates, Electrochemistry Communications, 2002, 4(3), 239-244.

P.P. Prosini et al., Determination of the Chemical Diffusion Coefficient of Lithium in $LiFePO_4$, Solid State Ionics, 2002, 148, 45-51.

F. Croce et al., A Novel Concept for the Synthesis of an Improved $LiFePO_4$ Lithium Battery Cathode, Electrochemical and Solid State Letters, 2002, 5(3), A57-A50.

I. Belharouak et al., Improved $LiFePO_4$ Cathode for Lithium-Ion Batteries, Presented at the 14th International Conference on Solid State Ionic's, Extended Abstract, Jun. 22-27, 2003, Monterey, California, USA, 2 pages.

F. Croce et al., Composite $Ag-LiFePO_4$ Cathode for Polymeric Lithium Batteries, The Electrochemical Society; http://www.electrochem.org/meetings/future/203/meetng.htm, 1 page.

A. D'Epifanio et al., Quartz iron Phosphate as New Lithium Intercalation Electrode, The Electrochemical Society; http://www.electrochem.org/meetings/future/203/meetng.htm 1 page.

W. Xu et al., LiBOB and Its Derivatives Weakly Coordinating Anions, and the Exceptional Conductivity of Their Nonaqueous Solutions, Electrochemical and Solid-State Letters, 2001, E1-E4, 4(1).

W. Xu et al., Ionic Conductivity and Electrochemical Properties of Lithium Orthoborate Salts, http://www.electrochem.org/meetings/past/200/abstracts/symposia/bla/0107.pdf, United States, Sep. 5, 2001.

International Search Report dated Mar. 25, 2004 in International Patent Application PCT/US03/27025, International Filing Date Aug. 28, 2003.

K. Xu et al., Lithium Bis(oxalato)borate Stabilizes Graphite Anode in Propylene Carbonate, Electrochemical and Solid State Letters, 2002, A259-A262, 5(11).

K. Xu et al., LiBOB as Salt for Lithium-Ion Batteries, A Possible Solution for High Temperature Operation, Electrochemical and Solid State Letters, 2002, pp. A26-A29, vol. 5(1).

W. Xu et al., Structures of Orthoborate Anions and Physical Properties of Their Lithium Salt Nonaqueous Solutions, Journal of the Electrochemical Society, 2003, E74-E80, 150(1).

T. Fujii et al., Application of LiBOB as an Electrolyte Salt for 4 V Class Lithium Ion Rechargeable Cells, whttp://www2.electrochem.org/cgi-bin/abs?mtg=202&abs=0203, United States.

* cited by examiner

BATTERY HAVING HIGH RATE AND HIGH CAPACITY CAPABILITIES

REFERENCE TO PRIOR FILED APPLICATIONS

This application is related to U.S. patent application Ser. No. 10/272,415 filed Oct. 15, 2002 and entitled "Fluorinated Carbon Active Material", now U.S. Pat. No. 7,052,802. This application is also related to U.S. patent application Ser. No. 10/612,439, filed Jul. 1, 2003, and entitled "Improved Positive Electrode Material for Lithium Ion Batteries", now U.S. Pat. No. 7,632,317, which claims priority to U.S. Provisional Application Ser. Nos. 60/423,953, filed Nov. 4, 2002, and entitled "Improved Cathode Material for Lithium Ion Batteries" and to 60/463,696, filed Apr. 16, 2003, and entitled "Improved Cathode Material for Lithium Ion Batteries." This application is also related to Ser. No. 10/652,547, filed Aug. 28, 2003, and entitled "Cathode Material for Lithium Ion Batteries", now abandoned, which claims the benefit of provisional application Ser. No. 60/463,580, filed Apr. 16, 2003, and entitled "Cathode Material for Lithium Ion Batteries." The disclosure of each of the above applications is incorporated herein in its entirety.

TECHNICAL FIELD

This invention relates to batteries and more particularly to batteries having a cathode with multiple active materials.

BACKGROUND

A variety of devices place conflicting demands on a battery. Implantable cardioverter defibrillators (ICDs) are an example of a device that place conflicting demands on a battery. For instance, an ICD needs a battery that can provide high rate performance when the ICD detects an arrhythmia. In response to detecting the arrhythmia, the ICD uses the battery to quickly charge capacitors. The energy from these capacitors is used to deliver a defibrillation shock to the patient. Defibrillation shocks are repeatedly delivered to the patient until the arrhythmia is no longer detected. The same ICD also needs a battery that can provide low rate performance. For instance, an ICD must continuously sense and monitor the condition of the heart and provide continuous or intermittent pacing. These monitoring and pacing functions draw low to medium current but require high capacity. As a result, there is a need for a battery that can provide both high rate and low rate/high capacity performance capabilities.

SUMMARY

A battery is disclosed. The battery has an electrolyte activating one or more anodes and one or more cathodes. At least one of the one or more cathodes includes a first active material and a second active material. The first active material and the second active material are selected such that the first active material recharges the second active material during discharge of the battery.

One embodiment of the battery includes or consists of fluorinated carbon ($CF_x$) as a first active material and includes or consists of one or more second active materials selected from the group consisting of lithium vanadium oxide, polypyrrole, $MoO_2$, $MoS_2$, $H_2V_3O_8$ and metal vanadium oxides represented by $M_yH_{1-y}V_3O_8$ where $0<y\leq1$ and M represents Na, Mg, Ba, K, Co, Ca and combinations thereof. In some instances, x is greater than 0.2, and/or less than 1.2 before the initial discharge of the battery. In another example, the second active material includes or consists of lithium vanadium oxide ($Li_{1+y}V_3O_8$). In some instances, y is greater than 0 and/or less than 0.3 before the initial discharge of the battery. One example of the lithium vanadium oxide includes $Li_{1.2}V_3O_8$.

Another embodiment of the battery includes or consists of one or more first active materials selected from the group consisting of: $CuCl_2$, and $LiCuCl_2$; and includes or consists of one or more second active materials selected from the group consisting of lithium vanadium oxide, $TiS_2$, polypyrrole, $MoO_2$, $MoS_2$, $MnO_2$, $V_2O_5$, $V_6O_{13}$, $H_2V_3O_8$, and metal vanadium oxides represented by $M_yH_{1-y}V_3O_8$ where $0<y\leq1$ and M represents Na, Mg, Ba, K, Co, and Ca and combinations thereof. In one example, the second active material includes or consists of lithium vanadium oxide ($Li_{1+y}V_3O_8$). In some instances, y is 0 and/or less than 0.3 before the initial discharge of the battery. One example of the lithium vanadium oxide includes $Li_{1.2}V_3O_8$.

Still another embodiment of the battery includes or consists of one or more first active materials selected from the group consisting of: $MnO_2$, and $V_2O_5$; and includes or consists of one or more second active materials selected from the group consisting of lithium vanadium oxide, $TiS_2$, polypyrrole, $MoO_2$, $MoS_2$, $V_6O_{13}$, $H_2V_3O_8$, and metal vanadium oxides represented by $M_yH_{1-y}V_3O_8$ where $0<y\leq1$ and M represents Na, Mg, Ba, K, Co, and Ca and combinations thereof. In one example, the second active material includes or consists of lithium vanadium oxide ($Li_{1+y}V_3O_8$). In some instances, y is 0 and/or less than 0.3 before the initial discharge of the battery. One example of the lithium vanadium oxide includes $Li_{1.2}V_3O_8$.

In some instances, the mass ratios of the one or more first active materials to the one or more second active materials in the cathode is greater than 10:90, or greater than 20:80 and/or less than 90:10, or less 80:20. Additionally, suitable ratios of the one or more first active materials ratios can be in a range of: 30:70 to 70:30 or in a range of 40:60 to 60:40.

Defibrillators that employ the batteries are also disclosed.

DETAILED DESCRIPTION

Figure 1:
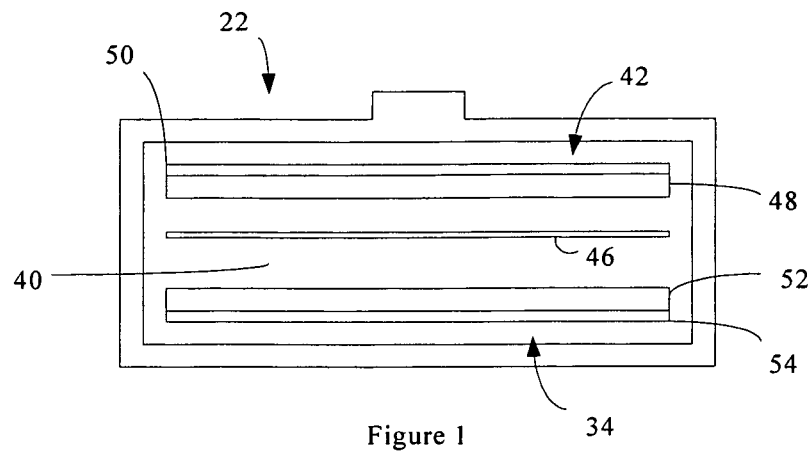
FIG. 1 is a schematic view of a battery.

A battery is disclosed. The battery includes a cathode having a first active material suitable for low rate applications and a second active material suitable for higher rate application. The combination of the high rate material and the low rate material makes the battery suitable for applications that require both high rate performance and low rate performance.

The second active material can be rechargeable. Additionally, the first active material and the second active material can be selected such that the potential of the first active material is above the potential of the second active material for all or a portion of the battery discharge. When the potential of the first active material is higher than the potential of a rechargeable second active material, the first active material can recharge the second active material. As a result, the battery can provide the high rate performance associated with the second active material and then recharge the second active material so the battery can again provide the high rate performance at a later time. Accordingly, the battery can be suitable for applications that require both high rate performance and high capacity performance.

Prior batteries have employed a cathode that includes silver in an active material such as silver vanadium oxide. However, without being bound to theory, it is believed that the silver enters the electrolyte from the cathode. This dissolution is believed to be a source of the adverse performance associated with these batteries during high rate applications. The disclosed batteries can include one or more cathodes with active materials that exclude silver and/or silver vanadium oxide. In some instances, the disclosed batteries include one or more cathodes with active materials that exclude silver and/or silver vanadium oxide. As a result, the battery can have a reduced level of dissolution associated with the cathode(s). Additionally, the exclusion of silver from the cathodes can reduce the costs associated with these batteries.

One example of the battery includes one or more first active materials selected from the group consisting of: fluorinated carbon ($CF_x$) $CuCl_2$, $LiCuCl_2$, $MnO_2$, and $V_2O_5$ and one or more second active materials selected from the group consisting of lithium vanadium oxide, $TiS_2$, polypyrrole, $MoO_2$, $MoS_2$, $MnO_2$, $V_2O_5$, $V_6O_{13}$, and metal vanadium oxides represented by $M_yH_{1-y}V_3O_8$ where $0<y\leqq 1$ and M represents Na, Mg, Ba, K, Co, and Ca and combinations thereof. The battery includes at least one second active materials that is different from at least one first active material. A first active material such as carbon monofluoride or fluorinated carbons ($CF_x$) provide low rate performance for long periods of time. Additionally, $CF_x$ is resistant to being oxidized and provides a low self-discharge at low depths of discharge. A second active material such as lithium vanadium oxide is capable of high rate performance and is easily recharged when compared with materials such as silver vanadium oxide. Additionally, lithium vanadium oxide can tolerate the stress due to repeated charging and recharging of the material. Further, lithium vanadium oxide is effectively recharged by $CF_x$.

FIG. 1 is a schematic view of a suitable battery 22. The battery 22 includes an electrolyte 40 activating a cathode 42 and an anode 44. A separator 46 separates the cathode 42 and anode 44. The cathode 42 includes a cathode medium 48 on a cathode substrate 50. The anode 44 includes an anode medium 52 on an anode substrate 54. Although the battery is illustrated as including one anode and one cathode, the battery can include more than one anode and/or more than one cathode with the anodes and cathodes each separated by a separator. Additionally, the battery can have a variety of different configurations such as stacked configuration, a "jelly-roll" or wound configurations. In some instances, the battery is hermetically sealed. Hermetic sealing can reduce entry of moisture into the battery. Moisture can react with the electrolyte and lead to corrosion and degradation of other battery components. Additionally or alternately, hermetic sealing can reduce entry of impurities into the battery. As a result, hermetic sealing can reduce active material degradation reactions due to impurities. The reduction in impurity induced lithium consumption can increase battery capacity.

The electrolyte 40 includes one or more salts dissolved in a solvent. The solvent can be an organic liquid or an inorganic liquid. The solvent can include or consist of one or more first solvents and/or one or more second solvents. In some instance, the first solvent is a low viscosity solvent and the second solvent is a high permittivity solvent. Examples of the first solvent include, but are not limited to, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy, 2-methoxyethane (EME), ethyl methyl carbonate (EMC), methyl propyl carbonate, ethyl propyl carbonate, diethyl carbonate (DEC), dipropyl carbonate, and mixtures thereof. Examples of second solvents include, but are not limited to, cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, y-butyrolactone (GBL), and mixtures thereof.

A preferred electrolyte includes one or more first solvents and one or more second solvents. Suitable ratios of the one or more first solvents to the one or more second solvents include, but are not limited to, ratios in a range of: 30:70 to 80:20. In a preferred example the ratio is in a range of 50:50 to 70:30.

Suitable salts for use with the electrolyte include, but are not limited to, alkali metal salts including lithium salts. Examples of lithium salts include $LiClO_4$, $LiBF_4$, $LiAsF_6$, $LiPF_6$, $LiSbF_6$, $LiCF_3SO_3$, $LiC_6F_5SO_3$, $LiC(CF_3SO_2)_3$, $LiN(SO_2C_2F_5)_2$, $LiN(SO_2CF_3)_2$, $LiAlCl_4$, $LiGaCl_4$, $LiSCN$, $LiO_2$, $LiO_3SCF_3$, $LiO_2CCF_3$, $LiSO_6F$, $LiB(C_6H_5)_4$, Li-methide, Li-imide, lithium alkyl fluorophosphates, organoborate salts and mixtures thereof. Examples of suitable organoborate salts include, but are not limited to, lithium bis(chelato)borates including lithium bis(oxalato)borate (LiBOB) and lithium difluoro oxalato borate (LiDfOB). Examples of suitable organoborate salts are disclosed in U.S. patent application Ser. No. 60/565,211, filed on Apr. 22, 2004, entitled "Organoborate Salt in Electrochemical Device Electrolytes" and incorporated herein in its entirety. The electrolyte can be prepared such that the salt has a concentration greater than 0.1 M, 0.5 M or greater than 0.7 M and/or less than 1.5 M, less than 2 M, or less than 5 M. For instance, the electrolyte can include 0.8 M to 1.5 M $LiAsF_6$ or $LiPF_6$ in a 50:50 mixture, by volume, of propylene carbonate and 1,2-dimethoxyethane. Another example of the electrolyte includes electrolyte 1.2 M $LiBF_4$ in a 30:70 by volume mixture of PC and DME.

In some instances, the electrolyte includes one or more additives. Additives can serve a variety of different functions. For instance, additives can enhance the ionic conductivity and/or enhance the voltage stability of the electrolyte. A preferred additive forms a passivation layer on one or more electrodes in the battery. The passivation layer can reduce further degradation of the electrolyte or electrodes. In one example, the passivation layer is formed by reduction of the additive at the surface of an electrode that includes carbon. In another example, the additive forms a polymer on the surface of an electrode that includes carbon. The polymer layer can serve as the passivation layer.

Suitable additives include, but are not limited to, carbonates, sulfur compounds, unsaturated hydrocarbons and nitrogen compounds. In some instances, the electrolyte includes at least one additive selected from the group consisting of: vinyl carbonate (VC), vinyl ethylene carbonate (VEC), ethylene sulfite, 1,3 dimethyl butadiene, styrene carbonate, aromatic carbonates, vinyl pyrrole, vinyl piperazine, vinyl piperidine, vinyl pyridine, and mixtures thereof. VC is an example of an additive that can be reduced to form a passivation layer that includes a carbonate at the surface of an electrode that includes carbon. Pyridine is an example of an additive that can form a polymeric passivation layer at the surface of an electrode that includes carbon. VEC is an example of an additive that can form a passivation layer by both being reduced and forming a polymer at the surface of an electrode that includes carbon. The concentration of additives in the electrolyte generally does not greatly exceed the concentration needed to form the passivation layer. As a result, the additives are generally present in smaller volume percentages than solvents. A suitable concentration for an additive in the electrolyte includes, but is not limited to, concentrations greater than 0.1 wt %, greater than 0.5 wt % and/or less than 5 wt %, less than 10 wt % or less than 20 wt %. In a preferred embodiment, the concentration of the additive is less than 3 wt %.

Suitable separators 46 include, but are not limited to, polyethylene, fabrics woven from fluoropolymeric fibers including polyvinylidine fluoride, polyethylenetetrafluoroethylene, and polyethylenechlorotrifluoroethylene used either alone or laminated with a fluoropolymeric microporous film, nonwoven glass, polypropylene, polyethylene, glass fiber materials, ceramics, polytetrafluoroethylene membrane, polypropylene/polyethylene membrane commercially available under the designation CELGARD (Celanese Plastic Company, Inc.), and a polyethylene membrane commercially available from Tonen Chemical Corp.

A suitable material for the anode substrate includes, but is not limited to, titanium, a titanium alloy, stainless steel, nickel, copper, tungsten, tantalum or alloys thereof.

The anode medium 52 includes or consists of one or more anode active materials and a binder. The anode active material can include or consist of a metal selected from Groups IA, IIA and IIIB of the Periodic Table of the Elements. Examples of these anode active materials include lithium, sodium, potassium, etc., and their alloys and intermetallic compounds including, for example, Li—Si, Li—Al, Li—B and Li—Si—B alloys and intermetallic compounds. Alternative suitable anode active materials include lithium alloys such as a lithium-aluminum alloy. The greater the amounts of aluminum present by weight in the alloy, however, the lower the energy density of the cell. Other alternative suitable anode active materials include graphite or other carbon, $Cu_6Sn_5$, $Cu_2Sb$, MnSb, other metal alloys, $Li_4Ti_5O_{12}$, silica alloys, or mixtures of suitable anode active materials.

In some instances, the anode consists of the anode medium. Accordingly, the anode medium can serve as the anode. For instance, the anode can include or consist of lithium metal or a lithium metal alloy. Lithium metal can be sufficiently conductive that an anode substrate is not necessary.

Suitable cathode substrates 50 include, but are not limited to, stainless steel, titanium, tantalum, platinum, aluminum, gold, nickel, or an alloy thereof.

The cathode medium 48 includes or consists of a plurality of cathode active materials and one or more binders. Suitable binders include, but are not limited to, carboxymethyl cellulose (CMC), powdered fluoropolymer, powdered polytetrafluoroethylene or powdered polyvinylidene fluoride. In some instances, the cathode medium includes a conductive diluent to further increase conductivity. Suitable diluents include, but are not limited to, acetylene black, carbon black and/or graphite or metallic powders such as powdered nickel and aluminum. In some instances, the cathode medium excludes a conductive diluent.

The cathode active materials include or consist of, one or more first active materials and one or more second active materials. In a preferred embodiment, the cathode active materials include or consist of, a first active materials and a second active material. The first active material is preferably a material capable of providing low rate performance over long periods of time. The second active material is a rechargeable material. In some instances, the first active material is not rechargeable. When the first active material is not rechargeable, the battery may function as a primary battery. When the first active material and the second active material are both rechargeable, the battery may function as a secondary battery.

Suitable first active materials include, but are not limited to, $CF_x$, $CuCl_2$, $LiCuCl_2$, $MnO_2$ and $V_2O_5$. In one embodiment, the first active material includes or consists of $CF_x$ where x can be greater than 0.2 and/or less than 1.2 before the initial discharge of the battery. Suitable second active materials include, but are not limited to, lithium vanadium oxide, $TiS_2$, polypyrrole, $MoO_2$, $MoS_2$, $MnO_2$, $V_2O_5$, and $V_6O_{13}$. In one embodiment, the second active material includes or consists of lithium vanadium oxide such as $Li_{1+y}V_3O_8$ wherein y can be greater than 0 and/or less than 0.3 before the initial discharge of the battery. One example of the lithium vanadium oxide includes $Li_{1.2}V_3O_8$.

One example of the cathode medium includes or consists of $CF_x$ as the first active material and lithium vanadium oxide, polypyrrole, $MoO_2$, $MoS_2$ or combinations thereof as the second active material. Another example of the cathode medium includes or consists of $CF_x$ as the first active material and lithium vanadium oxide as the second active material. Another example of the cathode medium includes $CuCl_2$, or $LiCuCl_2$, or combinations thereof as the first active material and lithium vanadium oxide, $TiS_2$, polypyrrole, $MoO_2$, $MoS_2$, $MnO_2$, $V_2O_5$, $V_6O_{13}$ or combinations thereof as the second active material. Yet another example of the cathode medium includes $MnO_2$, $V_2O_5$, or combinations thereof as the first active material and polypyrrole, $MoO_2$, $MoS_2$, $V_6O_{13}$ or combinations thereof as the second active material. Still another example of the cathode medium includes $CuCl_2$, $LiCuCl_2$, $MnO_2$, $V_2O_5$ or combinations thereof as the first active material and lithium vanadium oxide, polypyrrole, $TiS_2$, $MoO_2$, $MoS_2$ or combinations thereof as the second active material.

Suitable mass ratios of the one or more first active materials to the one or more second active materials in the cathode include, but are not limited to, ratios greater than 10:90, or greater than 20:80, or greater than 30:70 and/or less than 70:30, or less than 80:20, or less 90:10. Additionally, suitable ratios of the one or more first active materials ratios can be in a range of: 30:70 to 70:30 or 40:60 to 60:40. These ratios may change as function of the battery application. For instance, increased first active material can increase capacity but reduce rate capabilities.

To make a cathode, a mixture of the one or more first active materials, the one or more second active materials, a binder, a conductor, and water are mixed together to form a slurry. The slurry is applied to both sides of the cathode substrate and dried. In a preferred method, the one or more first active materials and the one or more second active materials are combined. A conductor such as carbon black can then be added and mixed. A binder such as polytrtrafluoroethylene (PTFE) can then be added and mixed. An additional binder such as carboxymethyl cellulose (CMC) in water can be added and mixed to form a slurry having the mass per cents of the one or more first active materials and the one or more second active materials as indicated above. A cathode substrate such as an aluminum substrate is coated with the slurry, dried by evaporation, and then pressed to the desired thickness.

Figure 2:
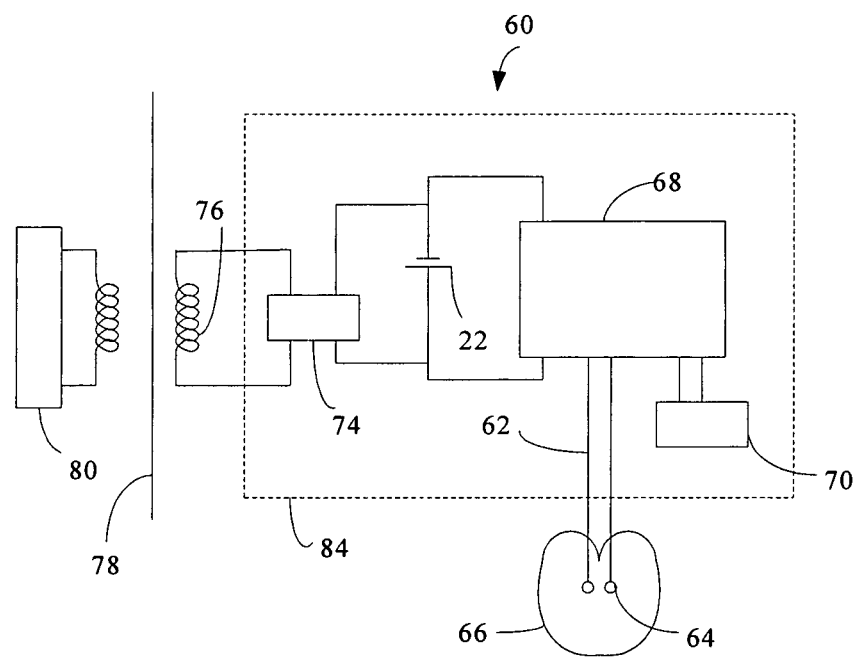
FIG. 2 is a schematic diagram of a defibrillation system.

The battery is suitable for use in a variety of implantable medical devices such as a defibrillator. FIG. 2 is a schematic diagram of a defibrillation system 60 that employs the battery. The defibrillation system 60 includes lead lines 62 connected to electrodes 64 in contact with the heart. Although the defibrillation system 60 is shown with two electrodes 64, the defibrillation system 60 may include three or more electrodes 64 and/or three or more lead lines. The specific positions of the electrodes 64 relative to the heart 66 is dependent upon the requirements of the patient. For instance, the electrodes 64 can be positioned in the superior vena cava and the right ventricle of the heart. Leads may be implanted in other regions of the heart such as the left atrium and left ventricle for therapies such as pacing for congestive heart failure.

The defibrillation system 60 also includes a processing unit 68. The lead lines 62 provide electrical communication between the processing unit 68 and the electrodes 64. The processing unit 68 is also in electrical communication with capacitor circuits 70. The capacitor circuits 70 are in electrical communication with the lead lines 62. The capacitor circuits 70 include one or more capacitors (not shown) for storing energy. The processing unit 68 can cause the one or more capacitors to be discharged such that energy stored in the one or more capacitors is delivered to the heart through all or a portion of the electrodes 64.

A battery 72 provides power to the processing unit 68 and the capacitor circuits 70. The battery 72 is in electrical communication with recharge circuits 74. The recharge circuits 74 are in electrical communication with a coil 76 positioned under the skin 78. The battery 72 can be charged by use of a radio frequency link between an external charger circuit 80 and the implanted recharge circuit 74. During charging of the battery 72, the external charger circuit 80 transmits energy from a coil through the skin 78 where it is received by the implanted coil 76. The implanted coil 76 supplies the energy to the implanted recharge circuit 74. The implanted recharge circuit 74 employs the energy to charge the battery 72.

Suitable processing units 68 can include, but are not limited to, analog electrical circuits, digital electrical circuits, processors, microprocessors, digital signal processors (DSPs), computers, microcomputers, or combinations suitable for performing the monitoring and control functions. In some instances, the processing unit 18 has access to a memory that includes instructions to be executed by the processing unit 18 during performance of the control and monitoring functions.

The processing unit 68, the battery 72, the capacitor circuits 70 and the recharge circuits 74 can be located within a case 84. Although the coil 76 is show as being positioned outside of the case 84, in some instances, the coil 76 can be positioned within the case 84.

During operation of the defibrillation system 60, the defibrillation system 60 employs output from the lead lines 62 to monitor the heart and diagnose when defibrillation shocks should be provided. These monitoring functions generally drain on the order of 10 μA from the battery 72. The defibrillation system 60 can also provide pacing capabilities. The current draw on a battery 72 due to constant pacing can be estimated by assuming that pacing will use 6-V, 500-μs pulses at an impedance of 500Ω at a rate of 70 beats/minute. Under these conditions, the energy drawn from the battery 22 will be about 2.5 mJ/min, or an average current draw of about 7 μA.

When the processing unit 68 identifies that defibrillation shocks are needed, the processing unit 68 provides the heart with one or more defibrillation shocks. To provide a defibrillation shock, the processing unit 68 employs energy from the battery 72 to charge the one or more capacitors in the capacitor circuits 70. The processing unit 68 causes these capacitors to be discharged such that energy stored in the capacitors is delivered to the heart through all or a portion of the electrodes 64 in the form of defibrillation shocks.

During the defibrillation shocks, the defibrillator requires that one or more pulses be delivered from the battery 72 to the one or more capacitors. Each pulse is generally associated with a defibrillation shock. The duration of each pulse is generally about 8 to 12 seconds with the pulses separated by about 8 to 12 seconds. In a preferred embodiment, each pulse has a duration of about 10 seconds and a separation of about 10 seconds. The defibrillator generally requires that each pulse provide at least 35 J to the one or more capacitors or at least 70 J to the one or more capacitors. In one embodiment, the defibrillator requires that each pulse provide at least 40 J to the one or more capacitors or at least 80 J to the one or more capacitors.

Although FIG. 2 illustrates the defibrillator having a single battery, the defibrillator can include more than one battery. For instance, the defibrillator can include a primary battery in addition to the battery. The primary battery can be employed to provide the energy needed for monitoring and pacing while the secondary battery can provide energy for the defibrillation shocks.

EXAMPLE 1

Cathodes were generated by mixing $CF_x$ with $x=1$, $Li_{1+y}V_3O_8$ with $y=0.2$, carbon black, PTFE and CMC to provide a slurry that was 36 wt % $CF_x$, 54 wt % $Li_{1+y}V_3O_8$, 5 wt % carbon black, 1.67% PTFE and 3.33% CMC. The slurry was coated on 20 um thick aluminum foil cathode substrate. The result was dried and pressed to a 30% to 50% porosity. Anodes were made from 250 μm thick lithium metal (Honjo metal co.).

An electrolyte was prepared by dissolving $LiBF_4$ to 1.2 M in a mixture having a PC:DME volume ratio of 30:70. Coin cells were prepared by employing the electrolyte to activate the anode and cathode with a polypropylene separator positioned between the anode and the cathode.

EXAMPLE 2

Figure 3:
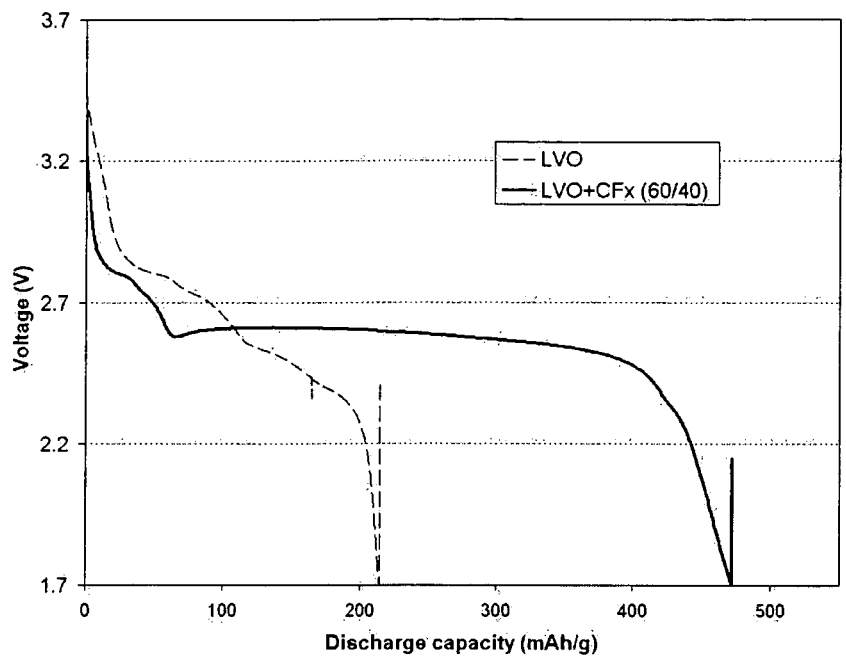
FIG. 3 presents the discharge profile for a battery having a cathode that includes fluorinated carbon and lithium vanadium oxide.

FIG. 3 presents voltage versus discharge capacity data for a coin cell from Example 1. The data was generated by discharging the cell at constant current at C/50 and at 37° C. FIG. 3 also presents voltage versus discharge capacity data for a cell having $CF_x$ as the only active material in the cathode.

EXAMPLE 3

Figure 4:
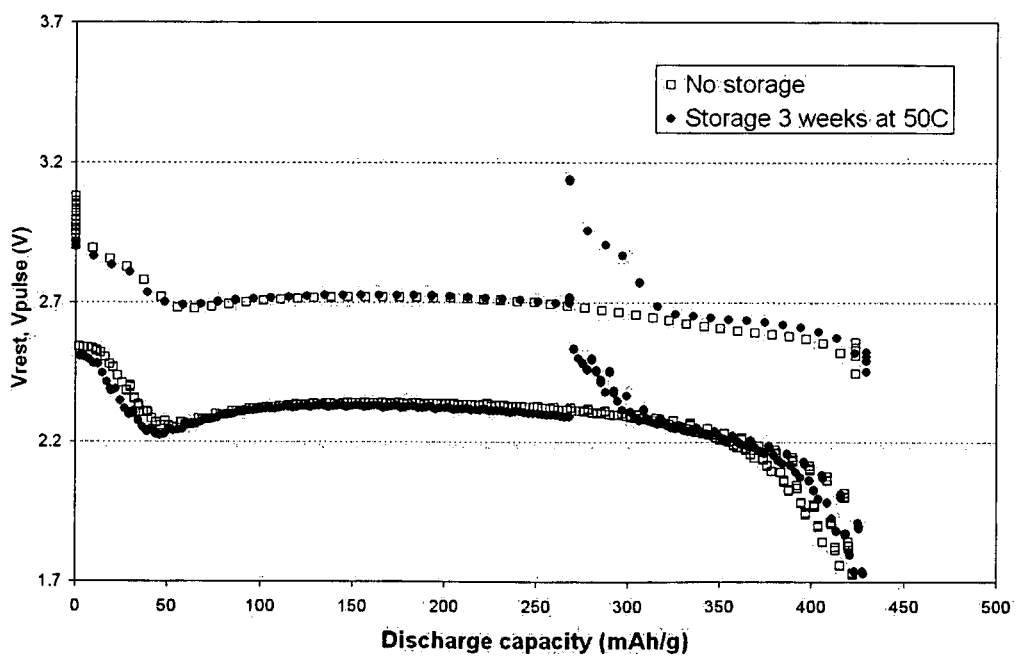
FIG. 4 presents the pulsing performance for a battery having a cathode that includes fluorinated carbon and lithium vanadium oxide.

The pulsing capability of the Example 1 coin cells was tested. Pulse trains were sequentially discharged from the cells at 37° C. Each pulse train included four pulses of 10 seconds each and separated by a 15 second rest. The pulse trains were separated by 30 minute rests. The results of this testing are presented in FIG. 4. FIG. 4 includes data for a first cell represented by the filled squares and data for a second cell represented by the hollow squares. The first cell was continuously discharged as described above without storage. The second cell was discharged as described above until reaching about a 60% depth-of-discharge when it was stored for about 3 weeks at 50° C. After storage, the discharge of the second cell was continued as described above.

The data for each of the cells includes an upper curve and a lower curve. The points of the upper curves represent the cell voltage before a pulse train is discharge. The points for the lower curves represent the lowest cell voltage during each pulse. Because there are four pulses in each pulse train, there are four times as many data points in the lower curves as in the upper curves.

The data for the second cell shows that the voltage returns from about 2.7 V to a little under 3.2 V after storage. The return in voltage results from the $CF_x$ recharging the lithium vanadium oxide during the storage of the second cell.

The pulsing conditions described above can approximate the demands placed on a battery when a defibrillator provides defibrillation shocks to a patient. The return in the voltage of the second cell indicates that after a similarly constructed battery provides one or more defibrillation shocks, the battery voltage may return to a higher voltage which would permit the battery to provide more power in the event defibrillation shocks are required again at a later time.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

We claim:

1. A battery, comprising:
an electrolyte activating one or more anodes and one or more cathodes, at least one of the one or more cathodes including fluorinated carbon as a first active material and lithium vanadium oxide represented by $Li_{1+y}V_3O_8$, wherein y is greater than 0 and/or less than 0.3, the at least one of the one or more cathodes including the fluorinated carbon and the lithium vanadium oxide before an initial discharge of the battery.

2. The battery of claim 1, wherein the lithium vanadium oxide includes $Li_{1.2}V_3O_8$.

3. The battery of claim 1, wherein the one or more cathodes exclude silver vanadium oxide before an initial discharge of the battery.

4. The battery of claim 1, wherein the active materials in the one or more cathodes exclude silver before an initial discharge of the battery.

5. The battery of claim 1, wherein the anode includes lithium before an initial discharge of the battery.

6. The battery of claim 1, wherein at least one of the one or more anodes includes a lithium metal.

7. The battery of claim 1, wherein the electrolyte includes one or more additives selected from the group consisting of vinyl carbonate (VC), and vinyl ethylene carbonate (VEC).

8. The battery of claim 1, wherein a mass ratio of the fluorinated carbon to the lithium vanadium oxide in the cathode is less than 90:10 before an initial discharge of the battery.

9. The battery of claim 1, wherein a mass ratio of the fluorinated carbon to the lithium vanadium oxide in the cathode is in a range of 30:70 to 70:30 before an initial discharge of the battery.

10. A defibrillator, comprising:
a battery having an electrolyte activating one or more anodes and one or more cathodes, at least one of the one or more cathodes end including fluorinated carbon as a first active material and lithium vanadium oxide represented by $Li_{1+y}V_3O_8$, wherein y is greater than 0 and/or less than 0.3, the at least one of the one or more cathodes includes the fluorinated carbon and the lithium vanadium oxide before an initial discharge of the battery;
one or more capacitors configured to store electrical energy from the battery in an amount sufficient to generate one or more defibrillation shocks; and
a processing unit configured to control the storage of electrical energy in the one or more capacitors and to control the discharge of the electrical energy from the one or more capacitors.

11. The defibrillator of claim 10, wherein the lithium vanadium oxide includes $Li_{1.2}V_3O_8$.

12. The defibrillator of claim 10, wherein the one or more cathodes exclude silver vanadium oxide before an initial discharge of the battery.

13. The defibrillator of claim 10, wherein the active materials in the one or more cathodes exclude silver before an initial discharge of the battery.

14. The defibrillator of claim 10, wherein the anode includes lithium before an initial discharge of the defibrillator.

15. The defibrillator of claim 10, wherein at least one of the one or more anodes includes a lithium metal.

16. The defibrillator of claim 10, wherein the electrolyte includes one or more additives selected from the group consisting of vinyl carbonate (VC), and vinyl ethylene carbonate (VEC).

17. The defibrillator of claim 10, wherein a mass ratio of the fluorinated carbon to the lithium vanadium oxide in the cathode is less than 90:10 before initial discharge of the battery.

18. The defibrillator of claim 10, wherein a mass ratio of the fluorinated carbon to the lithium vanadium oxide in the cathode is in a range of: 30:70 to 70:30 before initial discharge of the battery.

19. A battery, comprising:
an electrolyte activating one or more anodes and one or more cathodes, at least one of the one or more cathodes including fluorinated carbon as a first active material and lithium vanadium oxide represented by $Li_{1+y}V_3O_8$, wherein y is greater than 0 and/or less than 0.3, and the at least one of the one or more cathodes excluding silver vanadium oxide before an initial discharge of the battery.

20. The battery of claim 19, wherein the active materials in the one or more cathodes exclude silver.

21. The battery of claim 19, wherein the anode includes lithium before an initial discharge of the battery.

22. The battery of claim 19, wherein at least one of the one or more anodes includes a lithium metal.

23. The battery of claim 19, wherein the electrolyte includes one or more additives selected from the group consisting of vinyl carbonate (VC), and vinyl ethylene carbonate (VEC).

24. The battery of claim 19, wherein a mass ratio of the fluorinated carbon to the lithium vanadium oxide in the cathode is less than 90:10 before an initial discharge of the battery.

25. The battery of claim 19, wherein a mass ratio of the fluorinated carbon to the lithium vanadium oxide in the cathode is in a range of: 30:70 before an initial discharge of the battery.

26. A defibrillator, comprising:
a battery having an electrolyte activating one or more anodes and one or more cathodes, at least one of the one or more cathodes including fluorinated carbon as a first active material and lithium vanadium oxide iepresented by $Li_{1+y}V_3O_8$, wherein y is greater than 0 and/or less than 03, and the at least one of the one or more cathodes excluding silver vanadium oxide before an initial discharge of the battery;
one or more capacitors configured to store electrical energy from the battery in an amount sufficient to generate one or more defibrillation shocks; and
a processing unit configured to control the storage of electrical energy in the one or more capacitors and to control the discharge of the electrical energy from the one or more capacitors.

27. The defibrillator of claim 26, wherein the lithium vanadium is $Li_{1.2}V_3O_8$.

28. The defibrillator of claim 26 wherein the active materials in the one or more cathodes exclude silver.

29. The defibrillator of claim 26, wherein the anode includes lithium before an initial discharge of the defibrillator.

30. The defibrillator of claim 26, wherein at least one of the one or more anodes includes a lithium metal.

31. The defibrillator of claim 26, wherein the electrolyte includes one or more additives selected from the group consisting of vinyl carbonate (VC), and vinyl ethylene carbonate (VEC).

32. The defibrillator of claim 26, wherein a mass ratio of the fluorinated carbon to the lithium vanadium oxide in the cathode is less than 90:10 before initial discharge of the battery.

33. The defibrillator of claim 26, wherein a mass ratio of the fluorinated carbon to the lithium vanadium oxide in the cathode is in a range of 30:70 to 70:30 before initial discharge of the battery.

34. A battery, comprising:
an electrolyte activating one or more anodes and one or more cathodes, at least one of the one or more cathodes including fluorinated carbon as a first active material and lithium vanadium oxide represented by $Li_{1+y}V_3O_8$, wherein y is greater than 0 and/or less than 0.3, and the active materials in the one or more cathodes exclude silver before an initial discharge of the battery.

35. The battery of claim 34, wherein the anode includes lithium before an initial discharge of the battery.

36. The battery of claim 34, wherein at least one of the one or more anodes includes a lithium metal.

37. The battery of claim 34, wherein the electrolyte includes one or more additives selected from the group consisting of vinyl carbonate (VC), and vinyl ethylene carbonate (VEC).

38. The battery of claim 34, wherein a mass ratio of the fluorinated carbon to the lithium vanadium oxide in the cathode is less than 90:10 before initial discharge of the battery.

39. The battery of claim 34, wherein a mass ratio of the fluorinated carbon to the lithium vanadium oxide in the cathode is in a range of: 30:70 before initial discharge of the battery.

40. A defibrillator, comprising:
a battery having an electrolyte activating one or more anodes and one or more cathodes, at least one of the one or more cathodes including fluorinated carbon as a first active material and lithium vanadium oxide represented by $Li_{1+y}V_3O_8$, wherein y is greater than 0 and/or less than 0.3, and the active materials in the one or more cathodes exclude silver before an initial discharge of the battery;
one or more capacitors configured to store electrical energy from the battery in an amount sufficient to generate one or more defibrillation shocks; and
a processing unit configured to control the storage of electrical energy in the one or more capacitors and to control the discharge of the electrical energy from the one or more capacitors.

41. The defibrillator of claim 40, wherein the lithium vanadium is $Li_{1.2}V_3O_8$.

42. The defibrillator of claim 40, wherein the anode includes lithium before an initial discharge of the defibrillator.

43. The defibrillator of claim 40, wherein at least one of the one or more anodes includes a lithium metal.

44. The defibrillator of claim 40, wherein the electrolyte includes one or more additives selected from the group consisting of vinyl carbonate (VC), and vinyl ethylene carbonate (VEC).

45. The defibrillator of claim 40, wherein a mass ratio of the fluorinated carbon to the lithium vanadium oxide in the cathode is less than 90:10 before initial discharge of the battery.

46. The defibrillator of claim 40, wherein a mass ratio of the fluorinated carbon to the lithium vanadium oxide in the cathode is in a range of 30:70 to 70:30 before initial discharge of the battery.

* * * * *